(12) United States Patent
Bagchi et al.

(10) Patent No.: US 9,040,576 B1
(45) Date of Patent: May 26, 2015

(54) COMPOSITIONS FOR IMPROVED BODY COMPOSITION

(71) Applicants: Debasis Bagchi, Oakville (CA); John Doherty, Oakville (CA); Philip Apong, Oakville (CA); Vaishali Joshi, Oakville (CA); Jason Peters, Oakville (CA)

(72) Inventors: Debasis Bagchi, Oakville (CA); John Doherty, Oakville (CA); Philip Apong, Oakville (CA); Vaishali Joshi, Oakville (CA); Jason Peters, Oakville (CA)

(73) Assignee: Northern Innovations Holding Corp, Oakville, Ontario (CA)

( * ) Notice: Subject to any disclaimer, the term of this patent is extended or adjusted under 35 U.S.C. 154(b) by 0 days.

(21) Appl. No.: 14/178,272

(22) Filed: Feb. 12, 2014

(51) Int. Cl.
*A61K 31/385* (2006.01)
*A61K 31/12* (2006.01)

(52) U.S. Cl.
CPC ............... *A61K 31/385* (2013.01); *A61K 31/12* (2013.01)

(58) Field of Classification Search
USPC .............................................. 549/39; 514/440
See application file for complete search history.

(56) References Cited

U.S. PATENT DOCUMENTS

2011/0064720 A1* 3/2011 Amato ....................... 424/94.65

* cited by examiner

*Primary Examiner* — Kristin Vajda

(57) ABSTRACT

A nutritional supplement is provided comprising alpha-lipoic acid and curcumin. The nutritional supplement may be used for reducing weight or reducing weight gain, for reducing fat or reducing fat gain, for reducing loss in lean mass or maintaining lean mass, or for reducing loss of appetite or for maintaining appetite.

5 Claims, 5 Drawing Sheets

COMPOSITIONS FOR IMPROVED BODY COMPOSITION

FIELD OF THE INVENTION

The present invention relates generally to dietary supplements. Particularly, the present invention provides compositions comprising alpha-lipoic acid and curcumin and methods of using the compositions.

BACKGROUND OF THE INVENTION

The use of dietary supplements among individuals, including recreational and elite athletes, as well as sedentary individuals wishing to improve health parameters, has become increasingly popular due to studies suggesting efficacy. While there are many dietary supplements for diverse indications ranging from general health improvement (e.g. vitamins and minerals) to athletic performance improvement (e.g. creatine and beta-alanine), a large number of dietary supplements are taken for the purpose of improving body composition.

Depending on the goal of the individual, dietary supplements may be taken for the purpose of reducing or maintaining body weight; reducing or maintaining body fat; or maintaining or increasing lean body mass. Bodybuilders, in particular, as well as some athletes in sports with weight classes, engage in diet and exercise programs with varying phases some of which are more permissive to weight gain than others. In order to gain lean mass, or muscle, it is generally acknowledged that an excess of calories must be consumed above those expended—however, this often results in increases in fat mass as well. Alternatively, in order to lose weight, most of which is preferably fat, it is necessary to consume a deficit of calories—however, this often results in an undesirable loss of lean mass.

Most known dietary supplements benefit changes in body composition to a limited degree and/or at the cost of an accompanied unwanted change in body composition. Accordingly, there is a need for dietary supplements with improved effects on body composition.

SUMMARY OF THE INVENTION

In one embodiment of the invention, there is provided a composition comprising alpha-lipoic acid and curcumin.

According to another embodiment, there is provided a method of reducing weight or reducing weight gain in an individual, the method comprising administering a composition comprising alpha-lipoic acid and curcumin.

According to another embodiment, there is provided a method of reducing fat or reducing fat gain in an individual, the method comprising administering a composition comprising alpha-lipoic acid and curcumin.

According to another embodiment, there is provided a method of maintaining lean mass or reducing loss of lean mass in an individual, the method comprising administering a composition comprising alpha-lipoic acid and curcumin.

According to another embodiment, there is provided a method of maintaining appetite, increasing appetite, or reducing loss of appetite in an individual, the method comprising administering a composition comprising alpha-lipoic acid and curcumin.

According to another embodiment, there is provided a method of improving the characteristics of a nutritional supplement, the method comprising adding to said nutritional supplement a composition comprising alpha-lipoic acid and curcumin prior to ingestion of said nutritional supplement.

BRIEF DESCRIPTION OF THE DRAWINGS

Embodiments will now be described, by way of example only, with reference to the attached Figures, wherein.

DETAILED DESCRIPTION OF THE EMBODIMENTS

Figure 1:
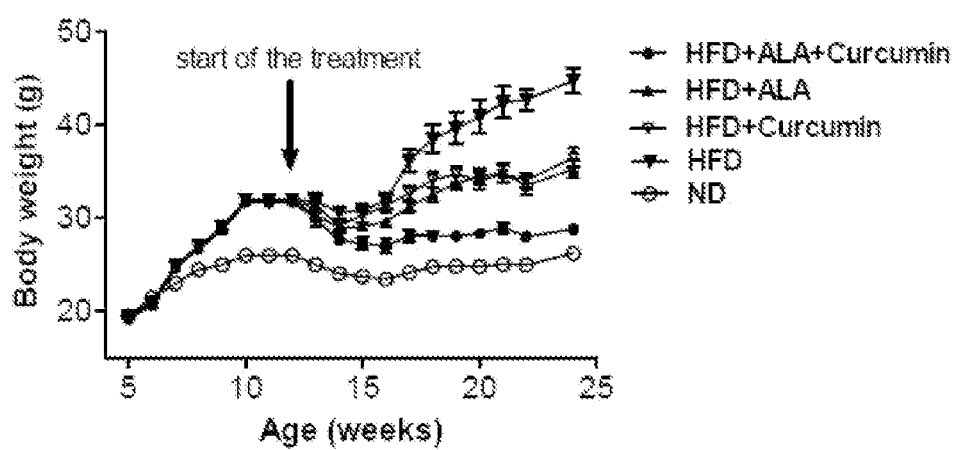
FIG. 1 shows the body weight of the mice during the course of the experiment.

A used herein, the terms 'composition' or 'nutritional composition' includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, 'nutritional compositions' as disclosed herein belong to category of compositions having at least one physiological function when administered to a mammal by conventional routes of administration.

Alternatively, formulations and nutritional compositions belonging to the present invention may be considered to be nutraceuticals. As used herein, the term 'nutraceutical' is recognized and used in the art to describe a specific chemical compound or combination of compounds found in, organic matter for example, which may prevent, ameliorate or otherwise confer benefits against an undesirable condition. As is known in the art, the term 'nutraceutical' is used to refer any substance that is a food, a part of food, or an extract or derivative of food that is suitable for consumption by an individual and providing physiological benefit which may be medical or health-related. Furthermore, the term has been used to refer to a product isolated, extracted or purified from foods or naturally-derived material suitable for consumption by an individual and usually sold in medicinal forms, such as caplets, tablets, capsules, gel-caps and the like, not associated with food.

The inventors have found that combinations of alpha-lipoic acid and curcumin are effective for altering aspects of body composition. The combinations have beneficial and synergistic effects on a number of parameters relevant to body composition.

As used herein, the term "alpha-lipoic acid" is used interchangeably with lipoic acid and ALA and may refer to racemic mixtures or R-lipoic acid and to salts thereof. Lipoic acid (also known as alpha-lipoic acid, thioctic acid, or 6,8-dithio octanoic acid) is a nutrient essential for aerobic metabolism that the human body makes in minute quantities. Small amounts may also be obtained from dietary sources such as spinach, broccoli, liver, and yeast. It is an organosulfur compound that exists as two enantiomers, R-(+)/S-(−), with only the R-form found in nature. Oral administration of lipoic acid has been shown to increase blood and cellular levels of lipoic acid. Lipoic acid supplements are available as R-lipoic acid or as a racemic mixture and are primarily marketed as an antioxidant.

Alpha-lipoic acid, in some aspects, may be provided as a racemic mixture or alternatively as the R-lipoic acid isomer. Furthermore, in some aspects, alpha lipoic acid may be provided as a salt, with sodium salts being the most common. The daily dosage of alpha-lipoic acid in the composition is about 100 mg to about 2000 mg, or about 1.5 mg/kg to about 40 mg/kg. Preferred amounts of alpha-lipoic acid include about 13.33 mg/kg/day for humans or about 800 mg per day for a 60 kg individual.

In other aspects, the dosage of alpha-lipoic acid in the composition is in the range from about 100, 150, 200, 250, 300, 350, 400, 450, 500, 550 600, 650, 700 or 750 mg, to about 2000, 1900, 1800, 1700, 1600, 1500, 1400, 1300, 1200, 1150, 1100, 1050, 1000, 950, 900 or 850 mg. In other aspects, the dosage of alpha-lipoic acid in the composition is 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 mg.

Curcumin is the one of the main curcuminoids found in the Indian spice turmeric (*Curcuma longa*), which are phenols responsible for the yellow color of turmeric and have long been used in the food industry as food coloring. Traditionally, for therapeutic uses, turmeric has been used to treat a variety of conditions or disorders including pain, gastrointestinal, liver, and pulmonary, and has been used both orally and topically. Curcumin has been shown to have antioxidant, anti-inflammatory, antibacterial, and antiviral activity.

Curcumin, in some aspects, may be synthetically produced. In other aspects, curcumin may be isolated or derived from plant material, where it may be obtained from extracts of whole plant or from particular plant parts, preferably from rhizomes. Alternatively, curcumin may be obtained from unprocessed plant material. Curcumin may be obtained from different plant sources including *Curcuma longa, Curcuma aromatic, Curcuma zedoaria, Curcuma Phaeocaulis, Curcuma xanthorrhiza, Curcuma manga, Etlingera elatior, Costus speciosus*, and *Zingiber cassumunar*. Preferred plant sources include *Curcuma longa*. For extracts, preferred solvents include acetone, methanol, ethanol, isopropanol, hexane, and ethyl acetate; however, other suitable solvents may be used, which are known to those skilled in the art. Although other suitable extraction methods will be known to those skilled in the art, a typical extraction procedure is as follows. Dried rhizome is ground into powder and washed with a suitable solvent that extracts the color fraction containing curcumin, which may be distilled to obtain an oleoresin. The oleoresin is washed further using suitable solvents to extract the curcumin. Commercial turmeric preparations are available with curcumin contents ranging from about 3-98%. The daily dosage of curcumin is about 5 mg to about 1000 mg or about 0.06 mg/kg to about 20 mg/kg. Preferred amounts of curcumin is about 5 mg/kg/day for humans or about 300 mg per day for a 60 kg individual.

According to one embodiment, a composition is provided comprising alpha-lipoic acid and curcumin. The alpha-lipoic acid may be provided as R-lipoic acid or as a racemic mixture. The curcumin may be provided as purified curcumin, synthetic curcumin, or as a plant or plant extract. Preferred amounts of alpha-lipoic acid include about 13.33 mg/kg/day for humans or about 800 mg per day for a 60 kg individual. Preferred amounts of curcumin include about 5 mg/kg/day for humans or about 300 mg per day for a 60 kg individual.

In other aspects, the dosage of alpha-lipoic acid in the composition is in the range from about 400, 450, 500, 555, 600, 650, 700, 725 750 or 775 mg to about 1600, 1500, 1400, 1300, 1200, 1150, 1100, 1050, 1000, 950, 900, 875, 850 or 825 mg. In other aspects, the dosage of alpha-lipoic acid in the composition is about 400, 450, 500, 550, 600, 700, 725, 750, 775, 800, 825, 850, 875, 900, 950, 1000, 1050, 1100, 1150 or 1200 mg. In other aspects, the dosage of alpha-lipoic acid in the composition is in the range from about 5.0, 6.0, 7.0, 8.0, 9.0, 9.5, 10.0, 10.5, 11.0, 11.5, 12.0, 12.5, 13, or 13.25 mg/kg to about 50, 45, 40, 35, 30, 25, 20, 15, 14 or 13.5 mg/kg.

In other aspects, the dosage of curcumin in the composition is in the range from about 50, 100, 150, 200, 225, 250 or 275 mg to about 600, 550, 500 450, 425, 400, 375, 350 or 325 mg. In other aspects, the dosage of curcumin in the composition is about 50, 100, 150, 200, 225, 250, 275, 300, 325, 350, 375, 400, 450, 500, 550 or 600 mg. In other aspects, the dosage of curcumin in the composition is in the range from about 0.06, 0.08, 0.1, 0.2, 0.5, 1.0, 1.5, 2.0, 2.5, 3.0, 3.5, 4, or 4.5 mg/kg to about 20, 15, 10, 9, 8, 7, 6 or 5.5 mg/kg.

While the amounts of alpha-lipoic acid and curcumin in the composition should be as described above in order to be most effective, the ratio of the two may also be a factor in effectiveness. The ratio of alpha-lipoic acid to curcumin in the composition is preferably greater than 1 (i.e. more alpha-lipoic acid than curcumin). Preferably, the ratio is from about 2:1 to about 5:1, more preferably from about 2:1 to about 4:1. The most preferred ratio of alpha-lipoic acid to curcumin is about 2.67:1.

According to another embodiment, a composition comprising alpha-lipoic acid and curcumin is used in a method of reducing body weight of an individual. In some aspects the method is for reducing body weight gain or attenuating body weight gain in an individual, particularly when the individual is consuming a diet permissive to body weight gain or other circumstance permissive to body weight gain such as during periods of inactivity. Such a diet is frequently employed by individuals attempting to increase muscle, or lean mass, while minimizing weight gain. In such cases, increases in body weight are due to both increases in lean mass and fat mass, whereas the increased fat mass is incidental to increasing lean mass and generally undesired.

According to another embodiment, a composition comprising alpha-lipoic acid and curcumin is used in a method of reducing body fat of an individual. In some aspects the method is for reducing or attenuating body fat gain in an individual, particularly when the individual is consuming a diet permissive to body fat gain. Such a diet is frequently employed by individuals attempting to increase muscle, or lean mass, but wishing to minimize increases in body fat. In some aspects the method is for reducing body fat mass or for reducing gains in body fat mass in circumstances permissive to increases in body fat mass. In other aspects, the method is for reducing body fat percent (%) or for reducing gains in body fat % as might occur in situations where body fat mass is maintained while lean mass is increased, as is often desirable.

According to another embodiment, a composition comprising alpha-lipoic acid and curcumin is used in a method of attenuating loss of lean mass or of attenuating reductions in lean mass accrual in circumstances permissive to loss of lean mass or reductions in lean mass accrual. Circumstances permissive to loss of lean mass or reductions in lean mass accrual include, but are not limited to, being in a caloric deficit, periods of physical inactivity, and periods of over-excessive intense exercise. Such a circumstance may also include where an individual wishes to consume alpha-lipoic acid for a specific benefit but does not wish to experience the potential loss of lean mass or attenuated increase in lean mass accrual. Such circumstances also arise where individuals may reduce food intake and/or increase exercise volume/intensity in order to reduce body weight or fat mass while maintaining existing muscle mass. Individuals may also reduce food intake and/or increase exercise volume/intensity in order to maintain body weight or fat mass while attempting to increase lean mass.

According to another embodiment, a composition comprising alpha-lipoic acid and curcumin is used in a method of attenuating reductions in caloric intake in circumstances permissive to reduced caloric intake. Circumstances permissive to reduced caloric intake include, but are not limited to, loss of or reduction in appetite such as during illness or stress. Such a circumstance may also occur where an individual wishes to consume alpha-lipoic acid for a specific benefit but does not wish to experience the potential reduction in caloric intake as may arise when an individual does not wish to lose weight as may occur with reduced caloric intake.

According to another embodiment, a method of improving the characteristics of a nutritional supplement is used in which a composition comprising alpha-lipoic acid and curcumin is added to said nutritional supplement prior to ingestion of said nutritional supplement. By such addition, the nutritional supplement may be improved in one or more of the following characteristics: body weight gain reduction; body fat reduction; muscle increase; or lean mass increase.

EXAMPLE

Method. Based on the preferred dose in humans of about 13.33 mg/kg/day or about 800 mg per day for a 60 kg individual for alpha-lipoic acid and the preferred dose in humans of about 5 mg/kg/day or about 300 mg per day for a 60 kg individual for curcumin, diets for the mice were designed to provide the mice with the appropriate equivalent amounts of the required components for each of the experimental groups. The following formula for Human Equivalent Dose (HED) was used to calculate the dose for mouse diets:

$$HED = Animal\ Dose \times (Animal\ Weight/Human\ Weight)^{0.33}$$

for alpha-lipoic acid, $$800\ mg/kg = Animal\ Dose \times (0.025\ kg/60\ kg)^{0.33}$$

$$13.33\ mg/kg = Animal\ Dose \times (0.0766)$$

Animal Dose=174.02 mg/kg and for curcumin, $$300\ mg/kg = Animal\ Dose \times (0.025\ kg/60\ kg)^{0.33}$$

$$5\ mg/kg = Animal\ Dose \times (0.0766)$$

Animal Dose=65.27 mg/kg 5 week old C57BL6/J male mice were divided into 2 groups as follows: normal diet (ND) (10% kcal/fat) or high fat diet (HFD) (60% kcal/fat) each containing the same total calories. At 12 weeks of age, the HFD group was further divided into 4 groups as follows: HFD alone, HFD supplemented with alpha-lipoic acid (HFD+ALA), HFD supplemented with curcumin (HFD+CUR), or HFD supplemented with alpha-lipoic acid plus curcumin (HFD+ALA+CUR). Based on the average food intake, the daily dose for alpha-lipoic acid in the HFD+ALA group was about 174 mg/kg, the daily dose for curcumin in the HFD+CUR group was about 65 mg/kg, and the daily dose for each component in the HFD+ALA+CUR group was similar to that in the respective groups. Each of the 5 groups contained 8-10 mice. Body weight of the mice was recorded weekly and food intake was monitored every two days. After 10 weeks of treatment mice from each group were subjected to dual-energy X-ray absorptiometry (DEXA) scan; percent (%) body fat, fat mass, and lean mass were calculated.

Results. FIG. 1 shows the body weight of the mice during the course of the experiment. As expected the HFD mice exhibited increase in body weight compared to the ND mice. Each of the HFD+ALA and HFD+CUR weight gain less than the HFD mice. However, the HFD+ALA+CUR mice had a much greater inhibition of weight gain, which also appeared to be more stable over time.

Figure 2:
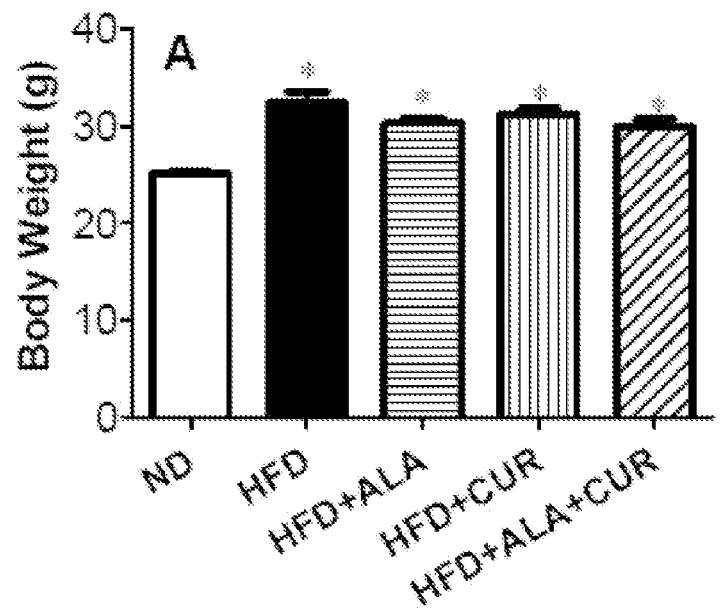
FIG. 2 shows the body weight of the mice before treatment.
Figure 3:
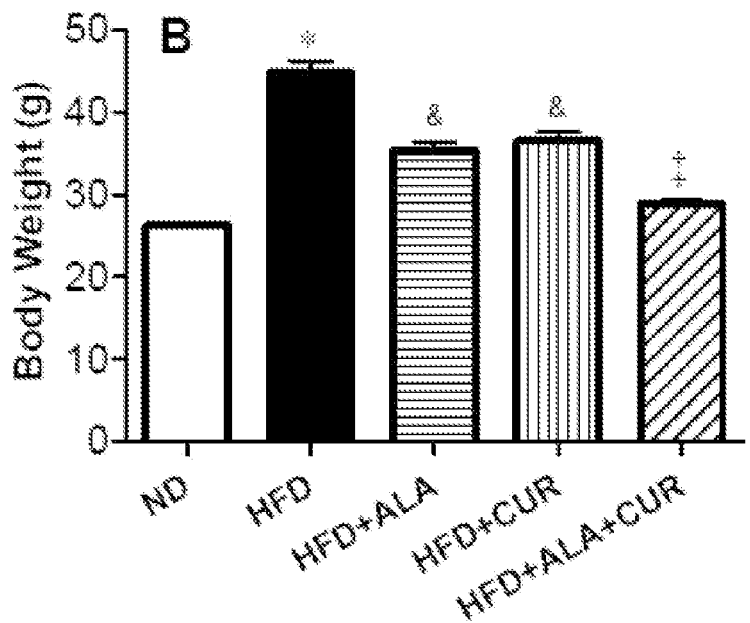
FIG. 3 shows the body weight of the mice after 11 weeks of treatment.

FIG. 2 shows the average weight prior to the start of treatment and FIG. 3 shows the average weight at the end of 11 weeks of treatment. Before treatment, all HFD mice had gained weight compared to ND mice. Following 11 weeks of treatment, either alpha-lipoic acid or curcumin alone attenuated weight gain, while alpha-lipoic acid combined with curcumin lead to a greater inhibition of weight gain compared to each of alpha-lipoic acid or curcumin alone. Note: for FIGS. 2 and 3 $*p<0.001$ compared to ND mice, $^\&p<0.001$ compared to HFD mice, $^\ddagger p<0.001$ compared to HFD+ALA mice.

Figure 4:
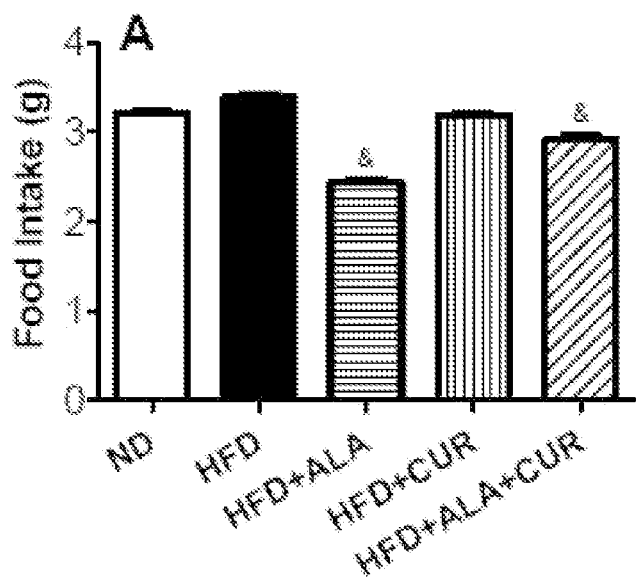
FIG. 4 shows the food intake (in grams) per day per gram body weight of the mice during the course of the experiment.
Figure 5:
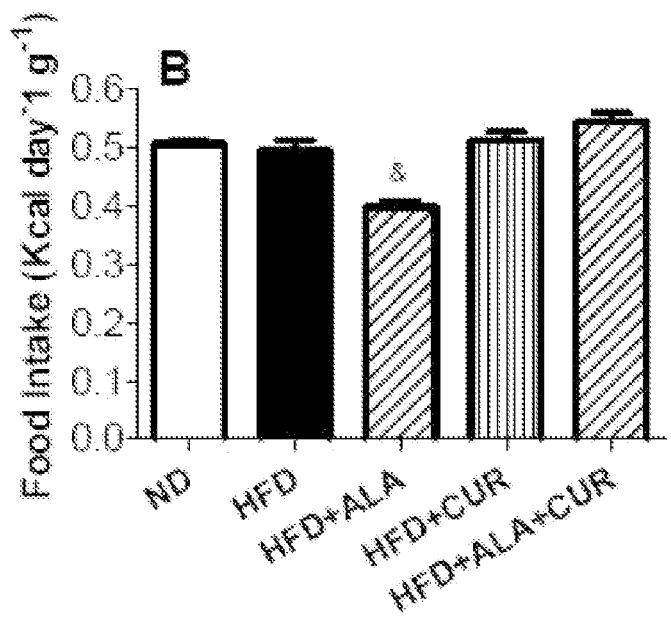
FIG. 5 shows the food intake (in kcals) per day per gram body weight of the mice during the course of the experiment.

FIGS. 4 and 5 show the food intake of the mice in grams and the food intake of the mice in terms of kcals consumed per day per gram body weight, respectively. Mice receiving alpha-lipoic acid alone or combined with curcumin exhibited reduced food intake, while reduced calorie intake was only observed in the alpha-lipoic acid group, suggesting that curcumin may attenuate or reverse the appetite-reducing effects of alpha-lipoic acid. Note: $^\&p<0.001$ compared to HFD mice.

Figure 6:
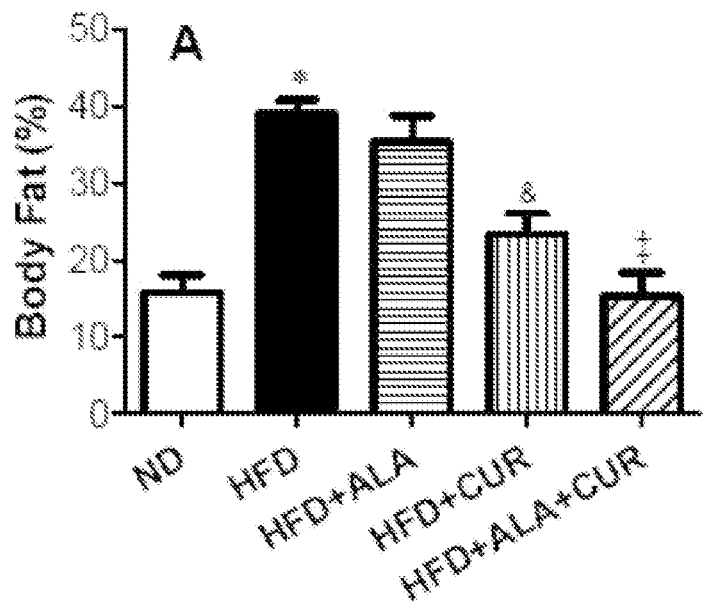
FIG. 6 shows the DEXA results for body fat % after 10 weeks of treatment.
Figure 7:
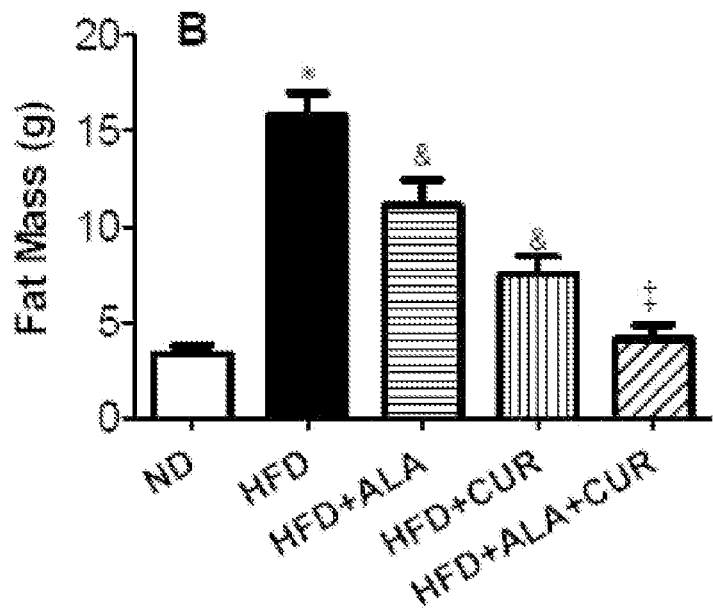
FIG. 7 shows the DEXA results for fat mass after 10 weeks of treatment.
Figure 8:
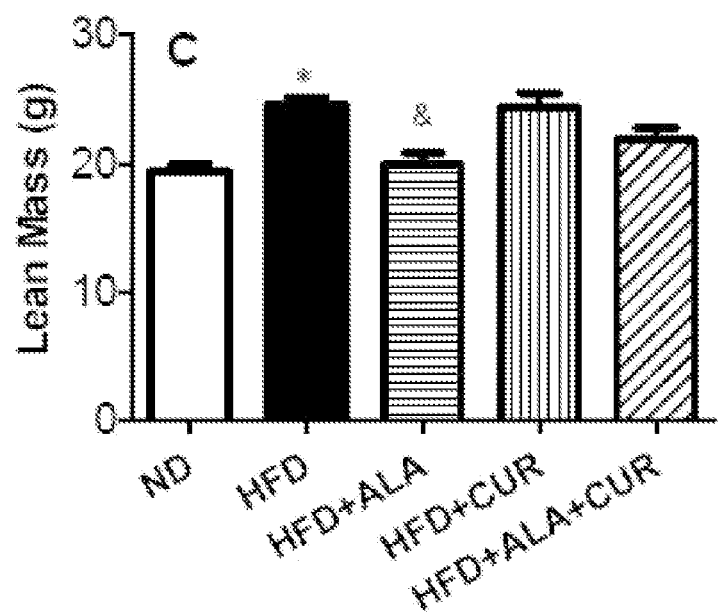
FIG. 8 shows the DEXA results for lean mass after 10 weeks of treatment.

FIGS. 6-8 show the results of DEXA analysis at the end of 10 weeks treatment. FIG. 6 shows the results for body fat %, FIG. 7 shows the results for fat mass (grams), and FIG. 8 shows the results for lean mass (grams). As expected, the HFD group showed significantly increased body fat %. Alpha-lipoic acid alone failed to reduce body fat %, while curcumin alone reduced the increased body fat % from a high fat diet. Interestingly, the combination of alpha-lipoic and curcumin exhibited near normal levels similar to the ND group. The effects on fat mass (FIG. 7) were similar to body fat %; however alpha-lipoic acid alone resulted in an attenuated increase in fat mass compared to the HFD group, albeit to a lesser degree than curcumin alone. Again, the combination of alpha-lipoic and curcumin exhibited near normal levels of fat mass. Lean mass was increased in the HFD group and was unaltered by treatment with curcumin alone or with alpha-lipoic combined with curcumin, while treatment with alpha-lipoic acid alone exhibited a significant attenuation in lean mass accrual (FIG. 8). Note: $*p<0.001$ compared to ND mice, $^\&p<0.001$ compared to HFD mice, $^\ddagger p<0.001$ compared to HFD+ALA mice.

Taking these results, the combination of alpha-lipoic acid with curcumin exhibits beneficial effects for different parameters of body composition, for some of which the combination exerts synergism, enhancement, or potentiation. While each of alpha-lipoic acid and curcumin show efficacy at attenuating weight gain in the context of diets permissive for gaining weight, the combination proved significantly more effective. Likewise, the combination proved significantly more effective for attenuating body fat mass and body fat % increases compared to either alpha-lipoic acid or curcumin alone.

In addition to the foregoing, the compositions of the present invention include formulations further comprising additional active ingredients and/or inactive ingredients, including solvents, diluents, suspension aids, thickening or emulsifying agents, sweeteners, flavorings, preservatives, solid binders, lubricants and the like, as suited to the particular dosage form desired. Except insofar as any conventional carrier medium is incompatible with the ingredients of the invention, such as by producing any undesirable effect or otherwise interacting in a deleterious manner with any other ingredient(s) of the formulation, its use is contemplated to be within the scope of this invention.

According to various embodiments of the present invention, the nutritional supplement may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage forms of the present invention are as a capsule, a tablet, or a caplet.

Furthermore, the dosage form of the nutritional supplement may be provided in accordance with customary processing techniques for herbal and nutritional supplements in any of the forms mentioned above. Additionally, the nutritional supplement set forth in the example embodiment herein may contain any appropriate number and type of excipients, as is well known in the art.

The above-described embodiments are intended to be examples of the present invention and alterations and modifications may be effected thereto, by those of skill in the art. The scope of the claims should not be limited by the preferred embodiments set forth in the examples, but should be given the broadest interpretation consistent with the description as a whole. It will be evident that various modifications and changes may be made thereto without departing from the broader spirit and scope of the invention.

All publications which are cited herein are hereby specifically incorporated by reference into the disclosure for the teachings for which they are cited.

What is claimed is:

1. A method of reducing body weight or body weight gain, comprising administering to a subject a composition comprising alpha-lipoic acid and curcumin.

2. A method of reducing body fat or body fat gain, comprising administering to a subject a composition comprising alpha-lipoic acid and curcumin.

3. A method of maintaining lean mass, comprising administering to a subject a composition comprising alpha-lipoic acid and curcumin.

4. A method of maintaining or increasing appetite, comprising administering to a subject a composition comprising alpha-lipoic acid and curcumin.

5. A method of maintaining or increasing caloric intake, comprising administering to a subject a composition comprising alpha-lipoic acid and curcumin.

* * * * *